United States Patent
König et al.

(10) Patent No.: US 9,754,127 B2
(45) Date of Patent: Sep. 5, 2017

(54) PROCESSING-CONTEXT-DEPENDENT PSEUDONYMIZATION OF SECURITY-CRITICAL MEDICAL DATA VIA A NETWORK

(71) Applicant: Siemens Aktiengesellschaft, Munich (DE)

(72) Inventors: Helmut König, Erlangen (DE); Andreas Pfeiffer, Nuremberg (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 556 days.

(21) Appl. No.: 14/225,723

(22) Filed: Mar. 26, 2014

(65) Prior Publication Data

US 2014/0379377 A1     Dec. 25, 2014

(30) Foreign Application Priority Data

Jun. 19, 2013   (DE) .................. 10 2013 211 540

(51) Int. Cl.
*G06F 21/62*   (2013.01)
*G06F 19/00*   (2011.01)
*G06F 21/00*   (2013.01)

(52) U.S. Cl.
CPC ........ *G06F 21/6254* (2013.01); *G06F 19/322* (2013.01); *G06F 21/00* (2013.01)

(58) Field of Classification Search
CPC .... G06F 19/322; G06F 21/00; G06F 21/6245; G06F 21/6254
See application file for complete search history.

(56) References Cited

U.S. PATENT DOCUMENTS

| | | | |
|---|---|---|---|
| 2007/0038437 A1* | 2/2007 | Brun | G06F 17/278 704/9 |
| 2007/0118550 A1* | 5/2007 | Yang | G06F 19/321 |

\* cited by examiner

*Primary Examiner* — Minnah Seoh
(74) *Attorney, Agent, or Firm* — Harness, Dickey & Pierce P.L.C.

(57) ABSTRACT

An apparatus, a method and a product for transferring security-critical medical data records via a public network are disclosed. In order to be able to transmit security-critical data sections in pseudonymized form, a pseudonymization function is adaptively applied to the data records. The pseudonymization function is in each case calculated dynamically on the basis of a processing context that has been read in and that takes account of the planned user role, the planned intended use of the data processing and an application context.

19 Claims, 4 Drawing Sheets

PROCESSING-CONTEXT-DEPENDENT PSEUDONYMIZATION OF SECURITY-CRITICAL MEDICAL DATA VIA A NETWORK

PRIORITY STATEMENT

The present application hereby claims priority under 35 U.S.C. §119 to German patent application number DE 102013211540.7 filed Jun. 19, 2013, the entire contents of which are hereby incorporated herein by reference.

FIELD

At least one embodiment of the present invention can be used in the fields of medical engineering and information technology and relates particularly to an approach for transmitting security-critical data records in pseudonymized form via a network.

BACKGROUND

In modern systems, the processing takes place in distributed fashion, so that the relevant data records need to be transmitted via a network to a receiver node on which the calculation steps are executed. This may also involve mobile nodes. Preferably, processing takes place in the cloud (headword: cloud computing). An essential aspect in this case is the available network bandwidth.

Medical data objects (e.g. image data and medical findings reports) contain a wealth of information that is relevant to protection (particularly protected health information, PHI data records for short) and that is meant to be accessible only to a specific group of recipients and not publicly, since these data can be used to identify the patient and other persons (such as doctors or relatives). For certain purposes, e.g. transmission of the data via a publicly accessible network, e.g. for the remote maintenance of appliances, it is therefore necessary to remove selected information from the data record in order to pseudonymize the data objects. This preparation of the data is demanded by security regulations.

To date, the data objects have been pseudonymized on the basis of predefined, fixed profiles that define what information needs to be removed from the data objects. This occurs uniformly and to a certain extent statically, since the edit context and purpose of subsequent data processing are not taken into account for the pseudonymization.

It is therefore important to perform necessary preprocessing steps (and also pseudonymization of the data records to be transmitted) such that it is possible to be flexible regarding the required transmission speed or the network bandwidth in order to be able to react dynamically and adaptively to technical transmission parameters for the data transmission of the network. If there is only a low network transmission capacity available, for example, it needs to be possible to calculate the preprocessing steps and particularly the pseudonymization using a variable computation specification such that in this case a higher degree of pseudonymization and hence a smaller volume of data needs to be transmitted. This solves the specific technical problem of adaptively allowing for the available network capacity during the pseudonymization and reducing the volume of data as far as possible depending on the applications.

It also needs to be possible to be able to execute the pseudonymization calculation on the basis of planned processing of the data on a receiver node. The reason is that it is relevant to pseudonymization whether the data to be transmitted are intended to be used to execute remote appraisal or whether the data are intended to be used for a clinical study (in which case, in contrast to the first application, the statement about the examination protocol used on the respective modality would be important; these data should then not be lost during pseudonymization and should be transmitted as well), for example.

SUMMARY

At least one embodiment of the invention relates to a method for transferring medical security-critical data records from a transmission station to at least one receiver station via a digital network, comprising:

capturing the medical security-critical data records to be transferred;

reading in a processing context for the medical security-critical data records;

dynamically calculating a pseudonymization function on the basis of the processing context that has been read in; and applying the determined pseudonymization function to the sections of the data records to be transferred that are determined as critical to security and producing a pseudonymized data record for the transfer.

In addition, at least one embodiment of the invention relates to an apparatus for transferring medical security-critical data records from a transmission station to at least one receiver station via a digital network, comprising:

an input data interface, configured to capture the security-critical data records to be transferred;

a context capture unit, configured to capture a planned processing context for the security-critical data records; and a processor, including a rulebook machine configured to store a multiplicity of predefinable and variable rules for dynamically calculating a pseudonymization function on the basis of the processing context that has been read in, configured to apply the determined pseudonymization function to the sections of the data to be transferred that are determined as critical to security and configured to produce a pseudonymized data record for the purpose of the transfer.

A further aspect of at least one embodiment of the invention relates to a computer program product that is designed to have a computer program, wherein the computer is prompted to perform the method according to at least one embodiment of the invention that is described above when the computer program is executed on the computer or on a processor of the computer.

A further aspect of at least one embodiment of the invention relates to a computer program having computer program code for performing all the method steps of the claimed or above-described embodiments of the method when the computer program is executed on the computer. In this case, the computer program may also be stored on a machine-readable storage medium.

A further aspect of at least one embodiment of the invention relates to a computer readable storage medium for storing the computer-implemented method described above and readible by a computer.

BRIEF DESCRIPTION OF THE DRAWINGS

The detailed description of the figures that follows discusses example embodiments—which are not intended to be understood as restrictive—with the features and further advantages thereof with reference to the drawing, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention relates to a method for transferring medical security-critical data records from a transmission station to at least one receiver station via a digital network, comprising:
the security-critical data records to be transferred are captured,
a planned processing context for the security-critical data records is read in,
a pseudonymization function is dynamically calculated on the basis of the processing context that has been read in,
the determined pseudonymization function is applied to those sections of the data to be transferred that are determined as critical to security and a pseudonymized data record is produced for the transfer.

In addition, at least one embodiment of the invention relates to an apparatus for transferring medical security-critical data records from a transmission station to at least one receiver station via a digital network, comprising:
an input data interface for capturing the security-critical data records to be transferred,
a context capture unit that is intended to capture a planned processing context for the security-critical data records,
a processor having a rulebook machine that stores a multiplicity of predefinable and variable rules for dynamically calculating a pseudonymization function on the basis of the processing context that has been read in, wherein the processor is intended to apply the determined pseudonymization function to those sections of the data to be transferred that are determined as critical to security and to produce a pseudonymized data record for the purpose of the transfer.

It is possible for data to be pseudonymized uniformly. By contrast, the pseudonymization solution of at least one embodiment of the present invention can match the pseudonymization to the planned use of the data and can perform said pseudonymization. An essential advantage is that more specifically relevant information can be obtained for the respective intended use, since fewer data are removed than is the case with generic pseudonymization. On the other hand, generic pseudonymization must take account of all conceivable cases (examples: for the intended use of remote maintenance of appliances, it makes sense to obtain the DICOM unique identifiers for study, series and instances). For the intended use for clinical studies (clinical trial scenario), on the other hand, determined diagnosis data records or medical details should be obtained (this also applies to the conditioning of image data for medical training purposes).

Since this specific, case-matched pseudonymization, if performed manually, would be a very time consuming and error-prone task for the user, the solution according to at least one embodiment of the invention with automated context-dependent pseudonymization of medical data holds important performance advantages. Furthermore, the security of the system can be increased. It is important that the network bandwidth can be taken into account dynamically when preparing the sending of the high-volume data records.

According to one advantageous embodiment of the invention, various aspects are taken into account in the processing context. At least the following aspects are automatically processed and taken into account for the calculation of the pseudonymization function:
a user role (with a plurality of users in a multiuser system, a plurality of user roles are accordingly also taken into account). Hence, the pseudonymization function is calculated on the basis of the user role that the user has for planned processing of the data on the receiver station.

An application context, particularly a medical workflow with an array of planned computer-based processing steps in the application context. Hence, the pseudonymization function is calculated on the basis of the array of computer-based processing steps.

An intended data use. Hence, the pseudonymization function is calculated on the basis of a planned intended use for the data to be transferred.

According to one aspect of at least one embodiment of the invention, intended data uses comprise at least the following uses:

use of the data in at least one clinical study,
use of the data for a remote service, particularly a technical service,
use of the data for remote medical appraisal.

The data record to be transferred is preferably a medical image data record, which is usually formatted on the basis of a DICOM protocol (DICOM: digital imaging and communications in medicine). The pseudonymization function that is applied to this data record (or to a plurality of data records) leaves a first section of the data record unaltered and pseudonymizes a second section of the data record, so that overall a pseudonymized data record is produced. In this case, there is no stipulation of, and it is dynamically determined, what the first or the second section must be. Advantageously, the respective subject of the first and the second sections is selected flexibly, so that the pseudonymization function is adaptively applied to various data record portions in order to match the context. It is important and advantageous that neither of the first and second sections needs to be a completely contiguous area in the data record.

By way of example it is thus possible for one portion of the image data to be used or defined as a first portion and for another portion of the image data with DICOM header data to be used or defined as a second portion, or vice versa. The pseudonymization function is basically calculated on the basis of the processing context, wherein the processing context is executed on or associated with the receiver station or at least on a further processing station associated therewith. Preferably, the dynamic calculation of the pseudonymization function is effected by accessing a predefinable rulebook. In this case, the rules can be changed (deleted, extended, modified) flexibly and also during operation. The respective medical, security-critical data record to be transferred comprises non-security-critical and security-critical sections, wherein the security-critical sections are automatically identified by way of PHI tags or elements for text structuring (e.g. XML elements and XML attributes).

The solution proposed here achieves dual dynamization for the pseudonymization of the data records:

1. Dynamic configuration is performed for which of the data sections in the data record actually need to be pseudonymized (for example, this first stipulates whether or not the "age" attribute needs to be pseudonymized). This determination takes place automatically using predefined rules. This determination is therefore adaptive and case-specific.
2. The actual pseudonymization is dynamically matched to the processing context when the pseudonymization function is calculated.

A further aspect of at least one embodiment of the invention relates to a computer program product that is designed to have a computer program, wherein the computer is prompted to perform the method according to at least one embodiment of the invention that is described above when the computer program is executed on the computer or on a processor of the computer.

A further aspect of at least one embodiment of the invention relates to a computer program having computer program code for performing all the method steps of the claimed or above-described embodiments of the method when the computer program is executed on the computer. In this case, the computer program may also be stored on a machine-readable storage medium.

A further aspect of at least one embodiment of the invention relates to a storage medium that is intended for storing the computer-implemented method described above and can be read by a computer.

It is within the scope of at least one embodiment of the invention for not all the steps of at least one embodiment of the method necessarily to have to be executed on one and the same computer entity, but rather for them also to be able to be executed on various computer entities. It is also possible for the order of the method steps of at least one embodiment to be varied if need be.

Furthermore, it is possible for individual sections of at least one embodiment of the method described above to be able to be executed in a saleable unit (e.g. associated with the transmission station) and for the remainder of the components to be able to be executed in another saleable unit (e.g. associated with the receiver station)—so to speak as a distributed system.

At this juncture, it is pointed out that the features, advantages and/or alternative embodiments that are claimed or described in this patent application in connection with the method can similarly also be transferred to the other claimed subjects and vice versa. In other words, the substantive claims (which are directed at an apparatus or at a product, for example) may also have been developed with the features described or claimed in connection with at least one embodiment of the method, and vice versa. The relevant functional features of at least one embodiment of the method are in this case produced by relevant substantive modules, particularly by microprocessor components or hardware modules.

An embodiment of the present invention relates to the preparation of medical data records for transfer via a digital network N. The transmission of security-critical data records via public networks (e.g. via the Internet) or within the context of cloud computing requires security-critical data sections to be camouflaged prior to the transmission, while the non-security-critical data sections are intended to be retained without alteration and in the original state. The pseudonymization is preferably effected by applying a pseudonymization function. What is essential is that the engineered pseudonymization function is no longer—as in the prior art—static, but rather that it is dynamic and hence can be flexibly matched to the respective application context.

By way of example, it is thus possible to calculate another pseudonymization function f depending on the application context.

The pseudonymization function f is used for pseudonymizing the data record that has been read in or captured. According to one aspect, pseudonymization means deleting or overwriting or rendering illegible identification features for which it is necessary to prevent or at least substantially hamper any inference (even if just indirectly through data processing processes) of the identification or the determination of the transmitter or affected party (patient). What is essential is that the identification features are no longer available in the data record (that is to say are not visible and also are no longer able to be read electronically). To this end, various measures can be taken. Firstly, these identification features can be deleted or they can be replaced by other data (without the possibility of identification) and hence altered (this process is also called anonymization). In the case of pseudonymization, it is possible to store a key that allows access to the pseudonymization function. The key can be used to apply an inverse pseudonymization function from the pseudonymized data record and thus to access the original data again. In this case, the pseudonymization function can also be applied inversely.

Furthermore, the calculation of the pseudonymization function f is matched to the planned use of the data to be transferred. In this case, it makes a difference whether the data to be transferred are intended to be used for a clinical study or for remote appraisal, for example. Depending on what intended use is planned, the pseudonymization function f needs to be calculated differently in order to be able to execute the later data processing in as targeted and optimum a fashion as possible.

The terms used within the scope of this application are explained in more detail below.

The method is used for transferring data records. The term "transfer" is intended to be interpreted in the sense of data transmission via a digital network. In this case, the data transfer takes place fully automatically and on a computer-aided basis. According to a further aspect, the transfer comprises preparation measures for secure electronic data transmission with pseudonymization.

On a lower level of the ISO-OSI layer model, the data transfer is based on a transport layer that fits on the network. In this case, the type of network is not limited to one particular type in principle. The network is usually a public digital network, such as the Internet, with known protocols for data interchange (e.g. http, https, etc.). According to another aspect the network relates to a LAN (local area network) network or a WLAN (wireless local area network) network. According to another aspect, the term "network" is intended to be understood in the sense of a mobile radio network or another wireless network for digital data transmission. Preferably, the network is used within the context of cloud computing. The transmission station and the receiver station are computer-based entities. There may however be individual computers or a complex of computers (such as a computer network, which may be built on the basis of different architecture principles). According to a further aspect, the transmission station and the receiver station are technical components of a computer and preferably are processors.

The term "security-critical data records" is an electronic or digital data record that preferably comprises medical data and may also contain image data, e.g. pixel data. The term can also be used in the plural synonymously (that is to say "security-critical data records" are dynamically preprocessed for network transmission). A data record is security-critical when it comprises data that needs to be protected. In this context, "data that needs to be protected" means that these data must not be sent via a public network.

The information contained therein comprises security-critical sections that need to be camouflaged prior to the transfer. Besides the security-critical sections, the security-critical data record may also comprise non-critical data that do not need to be preprocessed and treated further prior to transfer via a network. These non-security critical sections can be transmitted to a receiver node in unaltered form and preferably also in the original format. By way of example, non-security-critical data are time data, location data, institution data, software data, appliance data, etc.

Specifically which data sections need to be categorized as security-critical and non-security critical can be configured in advance. The rules for classification of security-critical data records can be altered on a variable basis. By way of example, it is thus possible for one application context to define different data sections as security-critical from another application context. Preferably, this can be mapped, converted and implemented using the proposed method.

Examples of security-critical data are preferably data that allow an identity of a patient to be inferred, such as the name of the patient, an identification number of the patient and possibly also further data sections, such as date of birth, type of illness, etc. The categorization of individual data sections takes place in advance for the security-critical data records too. Preferably, the categorization is performed fully automatically. This involves the use of PHI tags (PHI: protected health information) in particular. In one preferred embodiment, other mechanisms for automatically identifying security-critical sections in the security-critical data records are applied in this case. These include particularly mechanisms that are based on an OCR method (OCR: optical character recognition).

The term "processing context" relates particularly to planned processing of the data to be transferred on the receiver station. According to one aspect, the term "processing context" relates to a user role. The respective user on the receiver station may have different roles and may be registered on the computer system in these roles (e.g. as a doctor or as a nurse or as technical support, etc.). In this example embodiment, the type of user role thus defines the processing context. The pseudonymization function is then calculated on the basis of the respective user role.

In another aspect, the processing context relates to an application context. Application context means a context for the respective application. According to a further aspect, the application context relates to the planned data processing on the receiver station.

According to a further alternative, the application context relates to various application scenarios. By way of example, the application scenarios include an application as part of a clinical study, an application as part of remote services (in particular technical services) and/or application as part of remote diagnosis (e.g. as part of telemedical processing). Depending on what application scenario is executed or planned for the data to be transferred, a different processing context and hence also a different pseudonymization function are obtained.

According to a further aspect, the processing context is intended to be understood in the sense of an intended use for the planned processing on the receiver node. Depending on how the data are thus intended to be processed on the receiver node, the pseudonymization function is selected and calculated adaptively. The intended use is closely related to the application context. By way of example, it is thus possible for a first intended data use to be the processing of the data as part of a clinical study and for a second intended data use to be the processing of the data as part of remote appraisal or as part of technical maintenance. A particular workflow with an array of processing steps may be defined for this. This particularly involves accessing tools that allocate a particular set or array of computer-implemented applications to a sensed application context. If image data for a patient from a computer tomography examination of the brain are loaded, for example, then a particular array of evaluation tools can automatically be allocated. By way of example, in a first processing step, the captured image data can be presented on a display appliance. Furthermore, an application can be called that can be used to measure a tumor volume if an oncological application context is present. If there is no oncological application context present, the application for measuring the tumor volume, for example, makes no sense and is not executed in the first place. The invention involves this being automatically recognized and converted into electronic commands that are immediately executed on the computer.

Preferably, the processing context relates to planned and hence future processing on the receiver node. Alternatively it is also possible for the processing context to relate to processing on the transmission node. Furthermore, yet other processing contexts can be defined in other embodiments.

Usually, a rule machine is provided that keeps predefinable and variable rules for producing or calculating the pseudonymization function. The rules may comprise unimodal or multimodal input variables and are used to take the processing context that has been read in as a basis for adaptively and flexibly calculating a pseudonymization function that is then applied to the data to be transferred.

The pseudonymization function is used for pseudonymizing the security-critical sections from the data record. The security-critical sections are preferably PHI sections that are automatically identified. According to a first aspect, the pseudonymization is intended to be understood to mean camouflaging identification features in the data record. All data sections that indicate the identity of the data record or of the patient are replaced or possibly also deleted in accordance with the predefinable rules. By contrast, the non-critical sections are retained and can be transmitted without alteration. According to a further aspect, the pseudonymization is intended to be understood to mean anonymization, which involves the identified sections not being replaced but rather being deleted completely. Various methods can be applied for the specific execution of the pseudonymization. Thus, it is firstly possible for the security-critical content that is to be protected to be presented in a form concealed by graphical elements, for example (e.g. in the form of opaque bars). Alternatively the security-critical sections to be protected can be replaced by random data. In addition, it is possible for the security-critical sections to be deleted completely.

Figure 1:
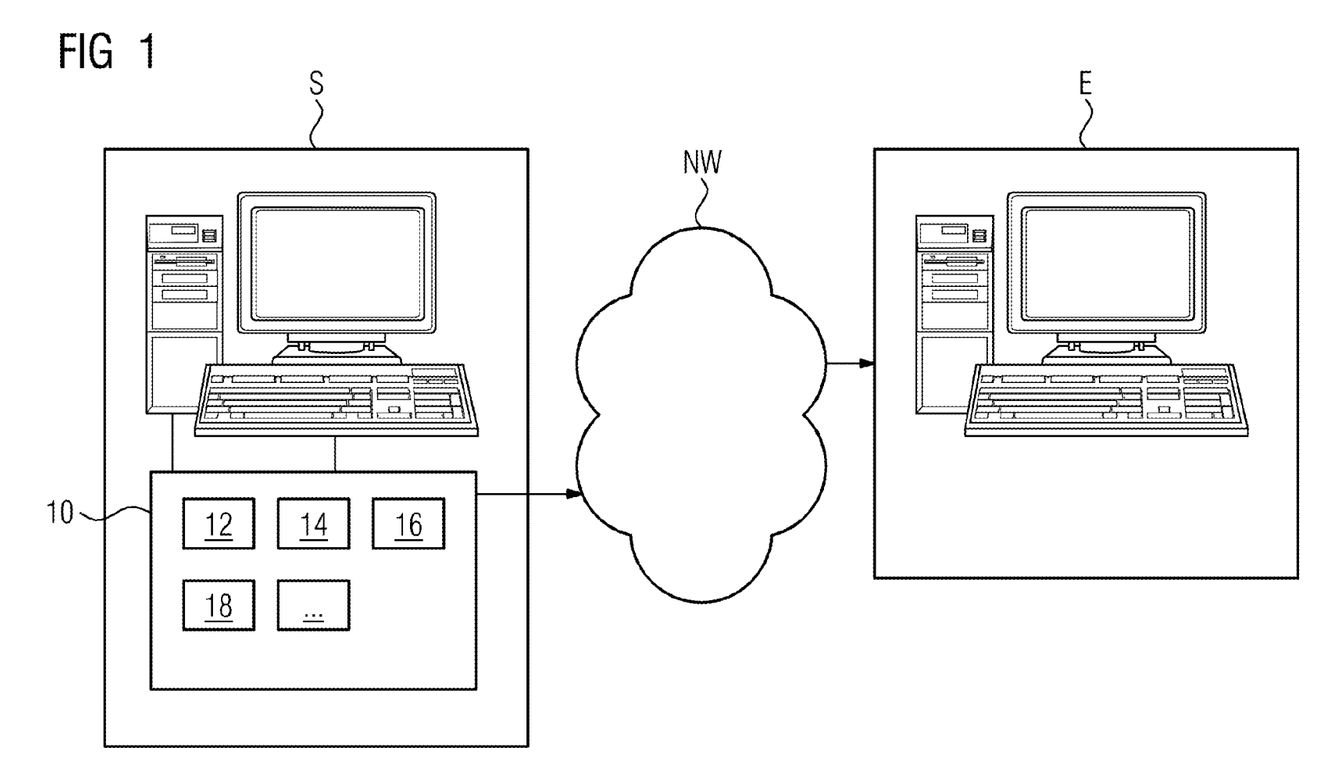
FIG. 1 shows an overview-like, schematic illustration of a digital network that is intended to be used to transmit security-critical, medical data records.

The basic architecture of the transfer system for adaptively pseudonymized data records is explained below with reference to FIG. 1.

A transmission station S is computer-based and may also be a computer network. The transmission station S comprises a transfer apparatus 10. The transfer apparatus 10 may be connected to the computer of the transmission station S as a separate module. Alternatively, the transfer apparatus 10 may be implemented as an add-on as part of a software implementation on the computer of the transmission station S. Before the medical data are forwarded via a public network NW to at least one receiver node or via a receiver station E, they need to be subjected to preprocessing that complies with the security rules. This is accomplished using the transfer apparatus 10.

The transfer apparatus 10 comprises an input data interface 12, a context sensing unit 14, a processor 16 and a rulebook machine 18. As indicated in FIG. 1 by the further box with the dots, the transfer apparatus 10 may also comprise further computer-implemented modules or components. By way of example, an additional compression unit for applying cryptological functions may also be provided in this case. In another preferred embodiment, additional measurement signal receivers and transmitters are also provided in this case, which denote technical parameters for the communication channel of the transmission network NW. By way of example, the available network bandwidth can be measured and forwarded to a rulebook cyclically or at predefined times.

The input data interface 12 is intended to sense the data records that are to be transferred. These can be produced directly on the transmission station S or read in thereon from other computer entities.

The context sensing unit 14 is intended to sense a planned processing context for the data records. The processing context preferably relates to planned processing on the receiver node or on the plurality of receiver nodes or stations on which the data are intended to be processed further. Preferably, the context sensing unit is an input interface in order to sense a user role, an application context and an intended use for the data.

The processor 16 is used for data processing. It may be part of the central data processing unit (CPU: central processing unit) of the station S, or it may be a separate module that is associated with the transmission station S. The transfer apparatus comprises a rulebook machine 18, in which a multiplicity of predefined rules that are variable during operation are intended for dynamic calculation of the pseudonymization function. As shown schematically in FIG. 1, it is possible for the rulebook machine 18 to be provided as a separate component in addition to the processor 16. In one preferred embodiment, the rulebook machine 18 is integrated in the processor 16, however. Furthermore, it is also possible for the parts of the transfer apparatus 10 that are described above to be integrated into a module.

Figure 2:
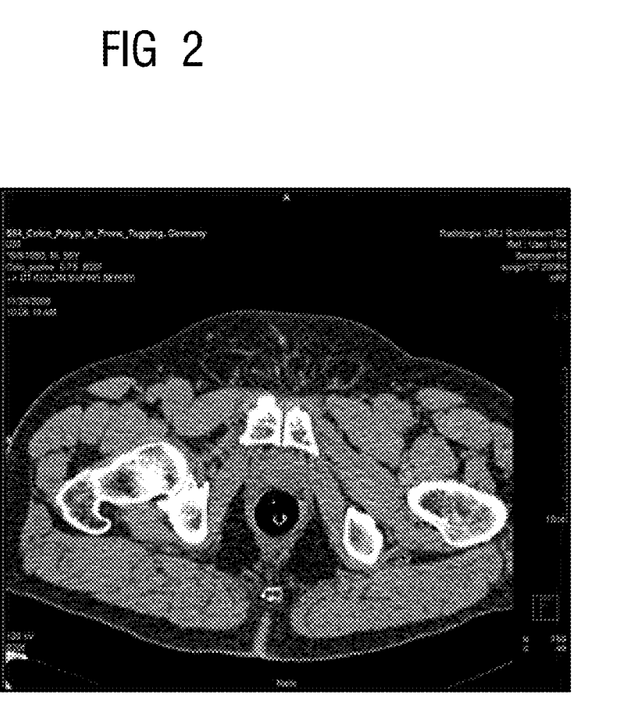
FIG. 2 shows a schematic illustration of a medical image data record that contains security-critical data that are intended to be adaptively pseudonymized using the method according to an embodiment of the invention prior to the transfer.
Figure 3:
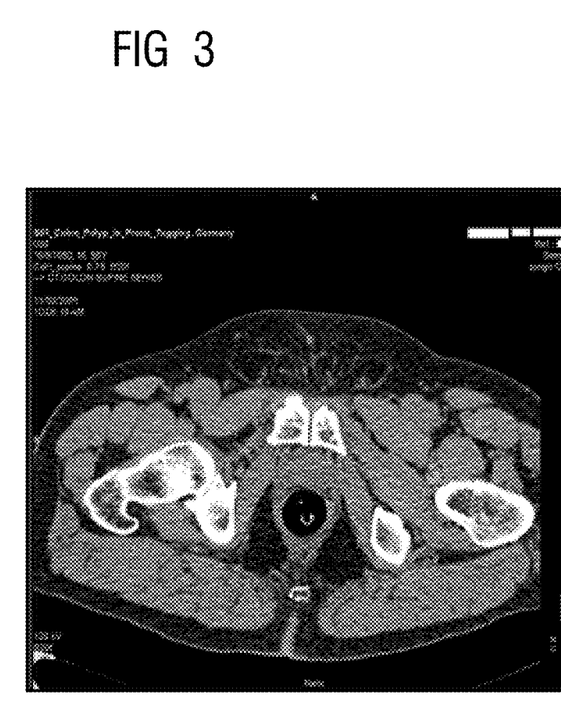
FIG. 3 shows the X-ray image already shown in FIG. 2, wherein a pseudonymization function has been applied, so that said X-ray image is presented in pseudonymized form.

FIG. 2 shows an example of a medical image data record that is intended to be forwarded via a public network NW to one or more receiver stations E. The data record comprises image data, non-critical and security-critical data, namely particularly such data as identify the respective patient (age, name, identification number, etc.). The security-critical data need to be pseudonymized prior to transfer. To this end, the data are forwarded to the transfer apparatus 10 for processing. When the data have been edited by the transfer apparatus 10, the pseudonymized data record that is shown by way of example in FIG. 3 is obtained. As a comparison of FIGS. 2 and 3 shows, the same image data records are found while individual sections from the DICOM header are presented only in pseudonymized form on the receiver node E. The pseudonymization can be effected by deleting the respective data records or by other camouflage. By way of example, it is thus possible to show a graphical element (in this case: a bar) instead of the security-critical data. However, it is essential that the security-critical data are not transported via the network NW in the original form. This has the advantage that it is not possible to infer the identity of the data owner even in the event of an attack on the network NW and in the event of the network traffic being monitored.

Figure 4:
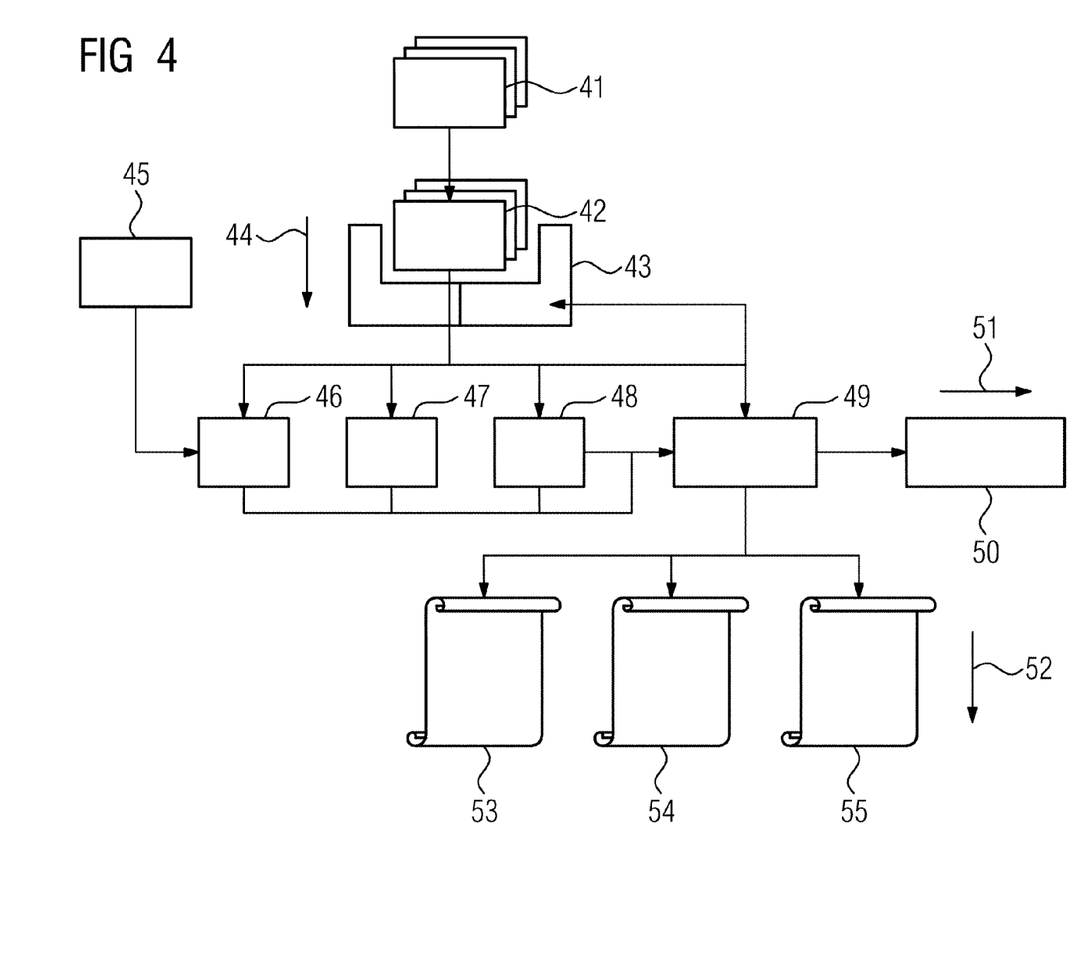
FIG. 4 shows a schematic overview of the software architecture according to an example embodiment of the invention.

FIG. 4 explains an example embodiment of an architecture in the manner of an overview. The respective application for processing the data records comprises a front end 41 and a back end 42. In this case, the application back end 42 accesses a workflow service 43. The front end 41 and the back end 42 are used to process an application content 44. The reference symbol 45 denotes a piece of service software, which for its part, accesses various toolkits, namely a web toolkit 46, an HL7 toolkit 47 and a DICOM toolkit 48. Other embodiments may naturally comprise further toolkits in this case. Following the toolkits and in interaction with the workflow service 43, a data export manager 49 is called, which for its part interacts with a user management system 50 (user management 50). The user management system 50 is used to define the user role 51. The data export manager 49 is busy at least to some extent with functionalities of the transfer apparatus 10 in this embodiment. Thus, it ascertains and processes the different processing context using the intended data use 52. In this embodiment, three application contexts are predefined:

1. a remote diagnosis configuration 53,
  2. a remote service configuration 54, and
  3. a clinical study configuration (clinical trials) 55.

It goes without saying that the processing context can also be extended with other configurations in other embodiments. The text below provides a more detailed explanation of aspects of the three different processing contexts that are relevant to pseudonymization.

1) Remote Diagnosis Processing Context 53

Examples that may be mentioned here are telemedicine, e.g. for obtaining a second opinion, and other applications in which the image is displayed. Besides metadata, pseudonymization also needs to take account of information in the pixel data. This aspect of the pseudonymization of medical image data is known. However, it is also true in this case that taking account of the context (purpose of use) allows targeted pseudonymization. In order to achieve better protection for the patient information, the pixel data from a DICOM image are additionally searched for relevant patient information. In this case, the contents of PHI-relevant tags from the DICOM header are recognized in the pixel data by way of an OCR (optical character recognition) engine and are then camouflaged. Which DICOM tags are included in this case is freely configurable.

2) Remote Service Processing Context 54

For this instance of application, technical parameters are at the heart of the concern and are used by service engineers to check the operability of appliances, such as modalities and workstations. For this, the pseudonymization function largely dispenses with medical information. Logical relationships between DICOM studies and DICOM series should be comprehensible in order to be able to comprehend the occurrence of errors for patients over time. For the technical parameters, private attributes (in particular manufacturer-specific technical information) need to be retained in the files. A similar situation applies to software test scenarios as a further processing context.

3) Clinical Trial Processing Context 55:

In this case, even after pseudonymization, certain medical data that are necessary for interpretation as part of the clinical study and for checking the association with a study group need to be retained under some circumstances (these are configurable by the user in a preparation step). Similarly, details regarding the examination protocol (e.g. protocols used on modalities) are regularly needed for imaging examinations. A similar situation applies to other research purposes and case study databases for medical training purposes (which is a further processing context).

All application back ends 42, including the service software 45, use toolkits (web toolkit 46, HL7 toolkit 47, and DICOM toolkit 48) in order to export data. These use the data export manager 49 in order to pseudonymize the data on a context-sensitive basis and transparently for the application.

As shown schematically in FIG. 4, the data pseudonymization is automated along the parameter axis user role, application context and intended data use. The system component that performs the automatic data pseudonymization is the data export manager. In FIG. 1, this corresponds to the transfer apparatus 10. The respective component asks the user management 50 what user role the logged-in user has (e.g. administrator or normal user with normal privileges or superuser with more privileges). The workflow service 43 is polled for which context the application is currently in. This is represented by way of example in FIG. 4 with the remote diagnosis context 53, the remote service context 54 and with the clinical study context 55. The pseudonymization is performed by way of the pseudonymization function f on the basis of the application context 53, 54, 55 and the intended data use 52. Depending on the context, a specific form of data pseudonymization is chosen that is based on one configuration. In this case, the application context can be extended by information relating to the intended use, which is linked to one or more work steps. A configuration contains details regarding content transformation (e.g. delete, replace). A content transformation may be based on DICOM supplement 142 "Clinical trial de-identification profiles", for example.

Figure 5:
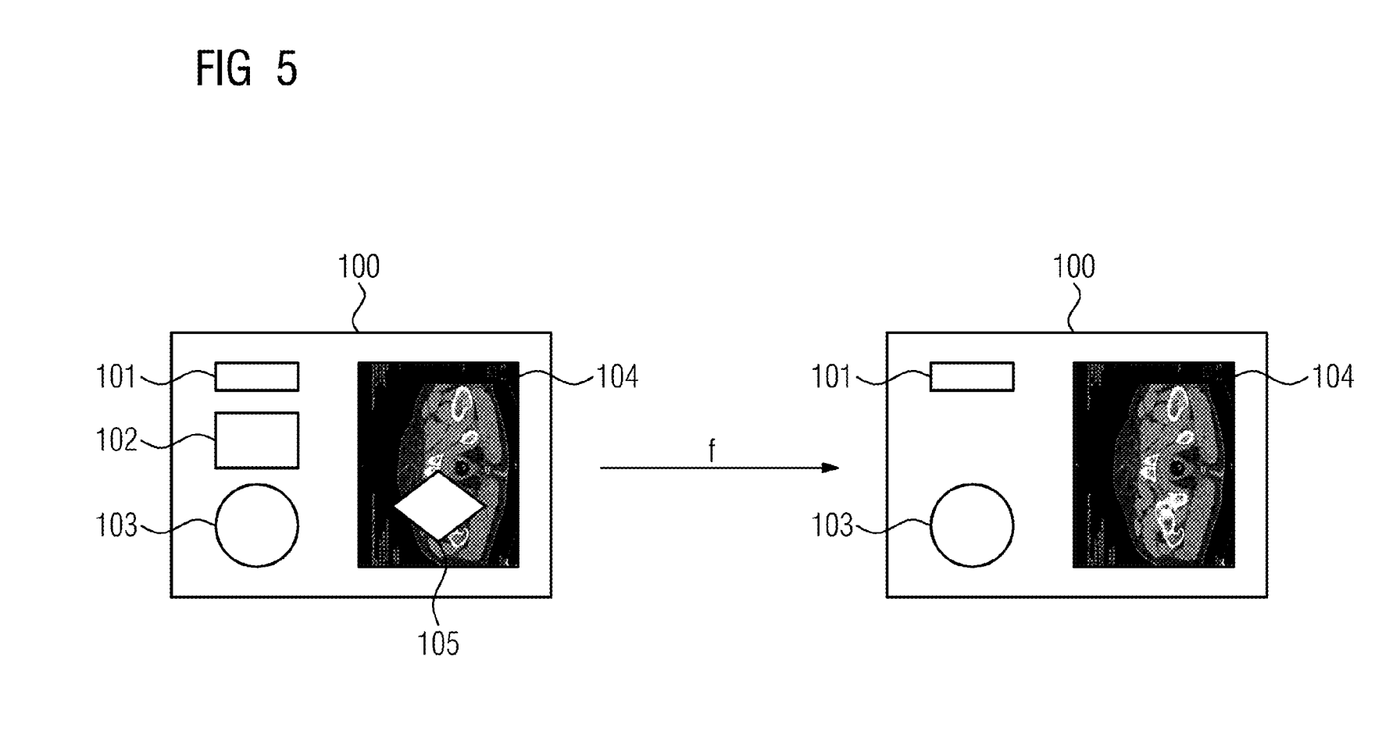
FIG. 5 shows a schematic illustration of an original image data record with security-critical data that is transferred by way of an adaptive pseudonymization function to a pseudonymized data record that is presented on the right-hand side.

FIG. 5 schematically shows an example of a data record that is to be transferred. On the left-hand side, the data record is shown in the original and is denoted by the reference symbol 100. The data record 100 is security-critical and comprises non-security-critical sections 101, 103 and 104, and also security-critical sections 102 and 105. In FIG. 5, the different sections are represented by different geographical shapes. The background of this is that the sections may be different data types. The individual sections do not necessarily have to be successive in a sequence but rather may be located at distributed positions in the respective data records. Furthermore, the individual sections may be differently formatted and may comprise text data, image data, audio data and further data types, for example. The pseudonymization function f transfers the original data record to a pseudonymized data record 200, which is shown on the right-hand side in FIG. 5. As can be seen in FIG. 5, the pseudonymized data record 200 no longer contains security-critical data sections. It merely comprises the non-security-critical data sections 101, 103 and 104. The data section 104 may be pixel data, for example.

Finally, it should be pointed out that the description of the invention and the example embodiments are fundamentally intended to be understood as nonrestrictive in respect of one particular physical implementation of the invention. In particular, it is evident to a person skilled in the art that the invention can be implemented to some extent or completely in software and/or hardware and/or in a manner distributed over a plurality of physical products—in this case particularly also computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

LIST OF REFERENCE SYMBOLS

S Transmission station
E Receiver station
NW Network
10 Transformation apparatus
12 Input data interface
14 Context sensing unit
16 Processor
18 Rulebook machine
41 Application front end
42 Application back end
43 Workflow service
44 Application context
45 Service software
46 Web toolkit
47 HL7 toolkit
48 DICOM toolkit
49 Data export manager
50 User management system/user management
51 User role
52 Intended data use
53 Remote diagnosis context
54 Remote service context
55 Clinical study context
100 Security-critical data record
200 Pseudonymized data record
f Pseudonymization function
102, 105 Security critical data sections
101, 103
104 Non-security critical data sections

What is claimed is:

1. An apparatus to transfer medical security-critical data records from a transmission station to at least one receiver station via a digital network, the apparatus comprising:

an input data interface configured to capture a medical security-critical data record to be transferred;

a context capture unit configured to capture a planned processing context for the medical security-critical data record;

a processor including a rulebook machine, the rulebook machine configured to store a multiplicity of variable rules for dynamically calculating pseudonymization functions, the rulebook machine further configured to be dynamically updated based on the captured planned processing context during operation of the apparatus;

wherein the processor is configured to execute computer-readable instructions to calculate a pseudonymization function based on the multiplicity of variable rules, apply the pseudonymization function to sections of the medical security-critical data record that are determined as critical to security, and produce a pseudonymized data record for transfer to the at least one receiver station; and wherein the captured planned processing context is indicative of a planned processing of the pseudonymized data record.

2. A method for transferring medical security-critical data records from a transmission station to at least one receiver station by a transfer apparatus via a digital network, the method comprising:

capturing a medical security-critical data record to be transferred;

capturing a planned processing context for the medical security-critical data record;

dynamically updating, during operation of the transfer apparatus, a rulebook machine based on the captured planned processing context, the rulebook machine storing a multiplicity of variable rules for dynamically calculating pseudonymization functions;

calculating a pseudonymization function based on the multiplicity of variable rules; and applying the pseudonymization function to sections of the medical security-critical data record that are determined as critical to security to produce a pseudonymized data record for transfer to the at least one receiver station; wherein the captured planned processing context is indicative of a planned processing of the pseudonymized data record.

3. The method of claim 2, wherein the captured planned processing context takes account of at least one of:

a user role that the user has for the planned processing of the pseudonymized data record at the at least one receiver station;

at least one of an application context and an array of computer-based processing steps; and a planned intended data use for the medical security-critical data record to the at least one receiver station.

4. The method of claim 3, wherein the planned intended data use comprises at least one of:

use of the medical security-critical data record in at least one clinical study;

use of the medical security-critical data record for a remote technical service; and use of the medical security-critical data record for remote medical appraisal.

5. The method of claim 2, wherein the medical security-critical data record includes a medical image data record.

6. The method of claim 2, wherein the sections of the medical security-critical data record include a first section and a second section;

the applying applies the pseudonymization function to only the second section, from among the first and second sections, to pseudonymize the second section of the medical security-critical data record to produce the pseudonymized data record; and the first section of the medical security-critical data record is left unaltered.

7. The method of claim 6, further comprising:

flexibly selecting the first or the second section so that the pseudonymization function is adaptively applied to various portions of the medical security-critical data record.

8. The method of claim 6, wherein the first and second sections in the medical security-critical data record are not successive; and neither the first nor the second section is a contiguous area in the medical security-critical data record.

9. The method of claim 2, further comprising:

executing the captured planned processing context on the at least one receiver station or at least one further processing station associated with the at least one receiver station.

10. The method of claim 2, wherein the calculating calculates the pseudonymization function by accessing the rulebook machine.

11. The method of claim 2, wherein the medical security-critical data record includes non-security-critical sections and security-critical sections; and the method further includes automatically identifying the security-critical sections by way of PHI tags or elements for text structuring.

12. The method of claim 2, wherein the pseudonymization function is based on an optical character recognition engine; and the method further includes executing the pseudonymization function by way of a de-identifier tool.

13. A computer program product, loadable or loaded into a memory of a computer-based transmission station, the computer program product comprising commands, readable by the computer-based transmission station, for executing the method of claim 2 when the commands are executed on the computer-based transmission station.

14. The method of claim 3, wherein the application context includes a medical workflow with an array of planned computer-based processing steps in the application context.

15. The method of claim 5, wherein the medical security-critical data record includes a medical image data record formatted based on a DICOM protocol.

16. The method of claim 6, wherein neither the first nor the second section is distributed in the medical security-critical data record.

17. The method of claim 7, wherein the first and second sections in the medical security-critical data record are not successive; and neither the first nor the second section is a contiguous area in the medical security-critical data record.

18. A non-transitory computer-readable storage medium storing computer-executable commands that, when executed on a computer-based transmission station, cause the computer-based transmission station to execute the method of claim 3.

19. A non-transitory computer readable medium including program code segments that, when executed on a computer, cause the computer to implement the method of claim 2.

* * * * *